United States Patent
Kuroda et al.

(12)

(10) Patent No.: US 6,414,169 B2
(45) Date of Patent: Jul. 2, 2002

(54) METHOD OF PRODUCING AN EPOXYCYCLODODECANE COMPOUND

(75) Inventors: Nobuyuki Kuroda; Junichi Kugimoto; Takato Nakamura; Nobuhiro Ii; Joji Funatsu, all of Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 09/783,920

(22) Filed: Feb. 15, 2001

(30) Foreign Application Priority Data

Feb. 15, 2000 (JP) ........................................ 2000-036160
Oct. 17, 2000 (JP) ........................................ 2000-316243

(51) Int. Cl.$^7$ ............................................. C09D 303/04
(52) U.S. Cl. ........................................ 549/540; 549/546
(58) Field of Search ................................. 549/540, 546

(56) References Cited

FOREIGN PATENT DOCUMENTS

SU            380650         5/1973

OTHER PUBLICATIONS

Russian Journal of General Chemistry, vol. 67, No. 6 (1997) P. 921–926.

*Primary Examiner*—Robert W. Ramsuer
*Assistant Examiner*—Andrea D'Souza Small
(74) *Attorney, Agent, or Firm*—Morgan, Lewis & Bockius LLP

(57) ABSTRACT

An epoxycyclododecane compound is produced by a catalytic hydrogenation reaction of 1,2-epoxy-5,9-cyclododecadiene, using a specific platinum-containing catalyst having a long life, under a hydrogen gas pressure of 0.8 to 9 MPa, and with a high yield of the target compound.

6 Claims, No Drawings

METHOD OF PRODUCING AN EPOXYCYCLODODECANE COMPOUND

BACKGROUND OF THE INVENTION

1. Field of the Invention

The present invention relates to a method of producing an epoxycyclododecane compound. More particularly, the present invention relates to a method of producing an epoxycyclododecane compound by catalytically and selectively hydrogenating double bonds of 1,2-epoxy-5,9-cyclododecadiene.

An epoxycyclododecane compound is useful for producing not only a resin component for paints and adhesives, but also a lactam compound, a lactone compound or a dibasic carboxylic acid through a cyclododecanone derived from the epoxycyclododecane by a conventional method and, thus, it is an important intermediate for polyamide 12 and polyesters which are useful materials for producing synthetic resins and synthetic fibers.

2. Description of the Related Art

It is known to produce an epoxycyclododecane compound by a catalytic reaction of 1,2-epoxy-5,9-cyclododecadiene with hydrogen in the presence of a platinum group metal-containing catalyst.

For example, Soviet Union (SU) Pat. No. 380,650 discloses a method of synthesizing an epoxycyclododecane compound by reducing 1,2-epoxy-5,9-cyclododecadiene with hydrogen in a cyclohexane medium in the presence of a catalytic component comprising a platinum-group metal (a metal of Group VIII of the Periodic Table) carried on a carrier consisting of alumina or activated carbon, at a reaction temperature of 70 to 200° C. under a hydrogen gas pressure of 101,325 to 263,445 kPa (100 to 260 atmospheres). In this method, however, the yield of the target epoxycyclododecane compound was 82 to 95% which was unsatisfactory. Also, this method is disadvantageous in that the necessary amount of the catalyst based on the amount of 1,2-epoxy-5,9-cyclododecadiene fed into the reaction procedure is too high.

Also, "Russian Journal of General Chemistry", Vol. 67, No. 6 (1997), pages 921 to 926, discloses a result of a reaction of 1,2-epoxy-5,9-cyclododecadiene with hydrogen in the presence of a catalyst comprising a catalytic component comprising a platinum group metal (for example, palladium or platinum) carried on a carrier component comprising an activated carbon, alumina or a silica gel. In an embodiment of the method, the reaction was carried out in the presence of a catalyst in which palladium is carried on a carrier comprising an activated carbon, alumina or a silica gel, at a reaction temperature of 30 to 90° C. under a hydrogen gas pressure of 0.1 to 4.0 MPa, and the target epoxycyclododecane compound was obtained in a yield of 80 to 99%. In another embodiment, the reaction was carried out in the presence of a catalyst in which platinum was carried on a silica gel carrier, at a reaction temperature of 50° C. under a hydrogen gas pressure of 1.3 to 2.5 MPa, and the target epoxycyclododecane compound was obtained in a yield of 84%. This report is, however, quite silent as to the length of the life of the catalyst.

Generally, when a catalyst containing a platinum group metal which is an expensive noble metal is used in industry, it is necessary that the resultant catalyst enables the target product to be produced in a high yield; the catalytic reaction can be effected at a high reaction rate; and the resultant catalyst has a long duration of life.

However, the prior art literature and patent publications did not teach or suggest how to impart a long life to the catalyst.

SUMMARY OF THE INVENTION

An object of the present invention is to provide a method which enables an epoxycyclododecane compound to be industrially produced with a high yield at a high reaction rate, by a reaction of 1,2-epoxy-5,9-cyclododecadiene with hydrogen in the presence of a catalyst with a long life thereof.

The above-mentioned object can be attained by the method of the present invention.

The method of the present invention for producing epoxycyclododecane compound comprises hydrogenating 1,2-epoxy-5,9-cyclododecadiene with a hydrogen gas in the presence of a platinum group metal-containing catalyst, the hydrogen gas having a pressure of 0.8 to 9 MPa, and the platinum group metal-containing catalyst being a platinum-containing catalyst.

In the method of the present invention for producing an epoxycyclododecane compound, the hydrogen gas pressure for the hydrogenation is in the range of from 3 to 7 MPa.

In the method of the present invention for producing an epoxycyclododecane compound, the hydrogenation is carried out under a hydrogen gas pressure of 0.8 to 9 MPa at a temperature higher than 50° C.

In the method of the present invention for producing an epoxycyclododecane compound, the platinum containing catalyst is employed in an amount, in terms of platinum, of 0.0005 times or less the molar amount of 1,2-epoxy-5,9-cyclododecadiene.

In the method of the present invention for producing an epoxycyclododecane compound, the platinum-containing catalyst comprises a platinum-containing catalytic component carried on an inert carrier component comprising at least one member selected from activated carbon, alumina, silica, silicaalumina, zeolite, and spinel.

In the method of the present invention for producing an epoxycyclododecane compound, the carrier component for the platinum-containing catalyst consists of activated carbon.

In the method of the present invention for producing an epoxycyclododecane compound, the platinum-containing catalytic component is present in an amount, in terms of platinum, of 0.1 to 10% by weight, based on the weight of the inert carrier component.

DESCRIPTION OF THE PREFERRED EMBODIMENTS

The 1,2-epoxy-5,9-cyclododecadiene usable, as a starting material, for the method of present invention can be produced by, for example, epoxidizing a cyclododecatriene with an organic carboxylic acid and hydrogen peroxide. In the resultant 1,2-epoxy-5,9-cyclododecadiene, the epoxy group and the double bond may be located in any of a cis-form, a trans-form or an other form.

For the method of the present invention, a trade 1,2-epoxy-5,9-cyclododecadiene may be employed without refining by distillation, etc., or after refining by distillation, etc. When the compound is a synthetic product, the compound is preferably employed after refining by distillation, etc.

The platinum-containing catalyst usable for the present invention is preferably selected from solid catalysts, preferably particulate solid catalysts, more preferably particulate solid catalyst having an average particle size of several μm to several hundreds μm, particularly 10 to 300 μm, comprising a catalytic component comprising a platinum-containing compound and carried on an inert carrier.

The inert carrier for the catalyst preferably comprises at least one member selected from the group consisting of activated carbon, alumina, silica, silicaalumina, zeolite and spinel, more preferably, activated carbon, alumina and silicaalumina. Still more preferably, the inert carrier is formed from activated carbon.

The platinum-containing catalytic component is preferably present in an amount, in terms of platinum, of 0.1 to 10% by weight, more preferably 0.2 to 8% by weight, based on the weight of the inert carrier component. In the catalyst, the platinum-containing catalytic component may be carried on the surface of and/or inside the inert carrier component.

In the method of the present invention, the specific platinum-containing catalyst exhibits a long life.

In the hydrogenation reaction of the method of the present invention, the platinum-containing catalyst is preferably used in a molar amount in terms of platinum, of 0.0005 times or less, more preferably 0.000001 to 0.0005 times, still more preferably 0.000005 to 0.0004 times the molar amount of 1,2-epoxy-5,9-cyclododecadiene used as a starting material. If the amount of the catalyst is too little, the time necessary to complete the reaction may be too long. Also, the use of the catalyst in too large an amount may cause the yield of the target product to decrease.

In the catalytic reaction of the method of the present invention, a reaction medium is not always necessary. When the reaction medium is used, for example, hydrocarbons, for example, n-hexane, n-heptane, n-tetradecane, and cyclohexane; ethers, for example, tetrahydrofurane and dioxane; alcohols, for example, methyl alcohol, ethyl alcohol, tert-butyl alcohol and tert-amyl alcohol; and esters, for example, ethyl acetate and butyl acetate, are employed. These organic compounds for the reaction medium may be employed alone or in a mixture of two or more thereof. The reaction medium is preferably employed in an amount of 0 to 20 times, more preferably 0 to 10 times, the weight of 1,2-epoxy-5,9-cyclododecadiene employed for the reaction.

In the method of the present invention, the hydrogenation for the double bonds of 1,2-epoxy-5,9-cyclododecadiene in the presence of the platinum containing catalyst is carried out under a hydrogen gas pressure of 0.8 to 9 MPa, preferably 1 to 8 MPa, more preferably 3 to 7 MPa. In the method of the present invention, the reaction temperature is not specifically limited. Preferably, the reaction temperature is preferably controlled to a level higher than 50° C., more preferably 70 to 200° C., still more preferably 70 to 150° C.

If the reaction hydrogen gas pressure and the reaction temperature are too low, a long time may be undesirably necessary to complete the reaction, and a yield of a by-product consisting of cyclododecanol may be increased, and the yield of the target compound may be decreased. Also, if the reaction hydrogen gas pressure and the reaction temperature are too high, an undesirable reduction of the target compound may be promoted and thus the yield of the target compound may be decreased.

In the method of the present invention, after the hydrogenation reaction procedure is completed, the catalyst is separated and recovered from the resultant reaction mixture, and the target epoxycyclododecane is isolated from the remaining reaction mixture by a refining means, for example, distillation. A high purity epoxycyclododecane is obtained. In the case where the resultant epoxycyclododecane is further converted to cyclododecanone or a dodecanedioic acid, after the catalyst is removed from the reaction mixture, the remaining reaction mixture may be subjected to an isomerization reaction of the epoxycyclododecane or to an oxidation reaction of the epoxycyclododecane contained in the remaining reaction mixture.

EXAMPLES

The present invention will be further explained by the following examples.

Example 1

An SUS Stainless steel autoclave having a capacity of 100 ml and equipped with a stirrer was charged with 20 g (0.112 moles) of 1,2-epoxy-5,9-cyclododecadiene and 0.08 g of platinum-containing catalyst particles comprising 5% by weight of a platinum-containing catalytic component carried on an activated carbon carrier (platinum atom amount: 0.0102 millimoles, water content: 50% by weight, BET specific surface area: 1200 $m^2/g$, made by N. E. CHEMCAT).

The inside of the autoclave was pressurized with a hydrogen gas to pressure of 5 MPa at room temperature. Then the reaction mixture was heated to a temperature of 70° C., and stirred at the above-mentioned temperature under the above-mentioned pressure until no absorption of hydrogen in the reaction mixture was established. After the reaction was completed, the reaction mixture was cooled to room temperature, the catalyst was removed from the reaction mixture by filtration, and the remaining reaction mixture was subjected to a gas chromatographic analysis.

In the results of the analysis, it was confirmed that the starting 1,2-epoxy-5,9-cyclododecadiene was completely consumed, the target epoxycyclododecane (which will be represented by ECD hereinafter) was produced in a yield of 99.6 molar %, and as by-products, cyclododecanone (which will be represented by CDON hereinafter) was produced in a yield of 0.04 molar %, cyclododecanol (which will be represented by CDOL hereinafter), was produced in a yield of 0.2 molar %, and cylcododecane (which will be represented by CDAN hereinafter) was produced in a yield of 0.04 molar %.

Examples 2 to 7 and Comparative Examples 1 to 3

In each of the Examples 2 to 7 and Comparative Examples 1 to 3, the epoxycyclododecane was produced by the same procedures as in Example 1, except that the type of the catalyst, the amount of the catalyst, the reaction temperature, the hydrogen gas pressure and the reaction time were controlled to those shown in Table 1. The analysis was carried out in the same manner as in Example 1.

The results are shown in Table 1.

TABLE 1

(Original)

| | | | | Reaction | | | | | | |
|---|---|---|---|---|---|---|---|---|---|---|
| | Catalyst | | Amount | Temperature | Hydrogen gas pressure | Time | Yield (molar %) | By-products | | |
| Example No. | Type | | (g) | (° C.) | (MPa) | (min) | ECD | CDON | CDOL | CDAN |
| Example | 1 | 5 wt % Pt/AC (*)$_1$ | 0.08 | 70 | 5 | 120 | 99.6 | 0.04 | 0.20 | 0.04 |
| | 2 | 5 wt % Pt/AC | 0.08 | 100 | 5 | 90 | 99.3 | 0.05 | 0.45 | 0.04 |
| | 3 | 5 wt % Pt/AC | 0.04 | 130 | 5 | 80 | 98.8 | 0.07 | 0.95 | 0.07 |
| | 4 | 5 wt % Pt/AC | 0.02 | 130 | 5 | 90 | 98.8 | 0.09 | 0.81 | 0.06 |
| | 5 | 0.5 wt % Pt/AN (*)$_2$ | 0.20 | 140 | 5 | 120 | 96.5 | 0.60 | 2.60 | 0.20 |
| | 6 | 5 wt % Pt/AC | 0.80 | 130 | 5 | 10 | 95.3 | 0.65 | 3.18 | 0.09 |
| | 7 | 2.5 wt % Pt/SI (*)$_3$ | 0.08 | 150 | 5 | 120 | 97.6 | 0.17 | 1.34 | 0.70 |
| Comparative | 1 | 5 wt % Pt/AC | 0.04 | 130 | 0.5 | 90 | 91.3 | 2.20 | 6.19 | 0.10 |
| Example | 2 | 0.5 wt % Pd/AC | 0.20 | 140 | 1 | 120 | 85.1 | 6.40 | 7.50 | 0.10 |
| | 3 | 0.5 wt % Pd/AN | 0.20 | 120 | 1 | 90 | 42.4 | 53.00 | 2.70 | 0.10 |

[Note]
(*)$_1$ AC . . . Activated carbon carrier
(*)$_2$ AN . . . Alumina carrier
(*)$_3$ SI . . . Silica carrier Example 8

A SUS stainless steel autoclave having a capacity of 1000 ml and equipped with a stirrer and a filter located at an outlet for a liquid fraction was charged with 500 g (2.8 moles) of 1,2-epoxy-5,9-cyclododecadiene and catalyst particles comprising 5% by weight of a platinum-containing catalytic component carried on activated carbon carrier particles (platinum atom amount: 0.128 millimoles, water content: 50% by weight, made by N. E. CHEMCAT). The inside of the autoclave was pressurized with a hydrogen gas to a pressure of 5 MPa. Then the reaction mixture in the autoclave was heated to a temperature of 130° C., and stirred at the above-mentioned temperature under the above-mentioned pressure for 2 hours.

After the reaction procedure was completed, the resultant reaction liquid fraction was withdrawn from the autoclave through the filter and subjected to the same analysis as in Example 1.

As a result, it was confirmed that the starting 1,2-epoxy-5,9-cyclododecadiene was completely consumed, the yield of ECD was 99.2 molar %, and as by-products, CDON was produced in a yield of 0.06 molar %, CDOL was produced in a yield of 0.70 molar %, and CDAN was produced in a yield of 0.04 molar %.

Then, the autoclave in which the filtered catalyst is remained was charged with 500 g (2.8 moles) of fresh 1,2-epoxy-5,9-cyclododecadiene, the reaction mixture was subjected to a reaction procedure at a temperature of 130° C. under a hydrogen gas pressure of 5 MPa for 2 hours. After the reaction procedure was completed, the resultant reaction liquid fraction was withdrawn from the autoclave through the filter, and subjected to the same analysis as in Example 1. The above-mentioned procedures were repeated 15 times. The test results are shown in Table 2. In the fifteenth reaction procedure, the starting 1,2-epoxy-5,9-cyclododecadiene was completely consumed, and no intermediate product, namely epoxycyclododecene (which will be represented by ECD hereinafter) was found in the withdrawn reaction liquid fraction.

The results are shown in Table 2.

TABLE 2

| Repeated reaction number | Catalyst | Yield (mol %) | | | | ECD' (*)$_4$ |
|---|---|---|---|---|---|---|
| | | ECD | CDON | CDOL | CDAN | |
| 1 | 5 wt % Pt/AC | 99.2 | 0.06 | 0.7 | 0.04 | 0 |
| 5 | 5 wt % Pt/AC | 99.2 | 0.05 | 0.59 | 0.05 | 0 |
| 10 | 5 wt % Pt/AC | 99.1 | 0.06 | 0.78 | 0.04 | 0 |
| 15 | 5 wt % Pt/AC | 99.0 | 0.07 | 0.89 | 0.05 | 0 |

[Note]
Reaction condition: ECD" (1,2-epoxy-5,9-cyclododecadiene: 500 g,
Catalyst: 5 wt % Pt/Activated carbon (AC) 1.0 g
Temperature: 130° C.
Pressure: 5 MPa
Time: 120 min.

Example 9

The same repeated reaction procedures as in Example 8 were carried out, except that the 1000 ml autoclave was replaced by a SUS stainless steel autoclave having a capacity of 100 ml and equipped with a stirrer and a filter; a catalyst comprising a catalyst component in an amount of 0.5% by weight, in terms platinum atoms, carried on alumina carrier particles was employed in an amount of 0.2 g; 1,2-epoxy-5,9-cyclododecadiene was employed in an amount of 20%; the reaction temperature was changed to 140° C.; and the repeated reaction number was 10 times.

The results are shown in Table 3.

TABLE 3

| Repeated reaction number | Catalyst | Yield (mol %) | | | | |
|---|---|---|---|---|---|---|
| | | ECD | CDON | CDOL | CDAN | ECD' (*)$_4$ |
| 1 | 0.5 wt % Pt/Alumina | 96.5 | 0.60 | 2.60 | 0.2 | 0 |
| 5 | 0.5 wt % Pt/Alumina | 93.0 | 1.10 | 4.30 | 0.50 | 0 |
| 10 | 0.5 wt % Pt/Alumina | 92.8 | 1.10 | 4.20 | 0.40 | 0 |

[Note]
ECD": 1,2-epoxy-5,9-cyclododecadiene
Reaction conditions: ECD": 20 g, 0.5 wt % Pt/Alumina catalyst: 0.2 g,
Temperature: 140° C.,
Pressure: 5 MPa,
Time: 120 min.

Comparative Example 4

The same reaction procedures and analysis as in Example 8 were carried out, except that the catalyst comprised 5 wt % of Pd-containing catalytic component carried on activated carbon particles; the reaction temperature was 50° C.; and the reaction time was 4 hours.

The results are shown in Table 4.

In the fifth reaction procedures, a large amount (36.2 molar %) of unreacted ECD" remained.

TABLE 4

| Repeated reaction number | Catalyst | Yield (mol %) | | | | |
|---|---|---|---|---|---|---|
| | | ECD | CDON | CDOL | CDAN | ECD' (*)$_4$ |
| 1 | 5 wt % Pd/AC | 95.9 | 0.64 | 2.62 | 0.66 | 0 |
| 5 | 5 wt % Pd/AC | 62.0 | 0.35 | 1.38 | 0.05 | 36.2 |

[Note]
AC . . . Activated carbon
ECD": 1,2-epoxy-5,9-cyclododecadiene
Reaction conditions: ECD": 500 g,
Catalyst: 5 wt % Pd/Ac: 0.5 g,
Temperature: 50° C.,
Pressure: 5 MPa,
Time: 240 min.

The method of the present invention enables an epoxycyclododecane compound to be produced by a catalytic hydrogenation reaction of 1,2-epoxy-5,9-cyclododecadiene at a high reaction rate with a high yield. The specific platinum-containing catalyst for the method of the present invention has a long life in practical use, and thus the method of the present invention has a high industrial utilizability.

What is claimed is:

1. A method of producing an epoxycyclododecane compound comprising hydrogenating 1,2-epoxy-5,9-cyclododecadiene with a hydrogen gas in the presence of a platinum group metal-containing catalyst, wherein the hydrogen gas has a pressure of 0.8 to 9 MPa, and wherein the platinum group metal-containing catalyst comprises a platinum-containing catalytic component carried on an inert carrier component consisting of activated carbon being employed in an amount, in items of platinum, of 0.000001 to 0.0005 times or less the molar amount of 1,2-epoxy-5,9-cyclododecadiene.

2. The method of producing an epoxycyclododecane compound as claimed in claim 1, wherein the hydrogen gas pressure for the hydrogenation is in the range of from 3 to 7 MPa.

3. The method of producing an epoxycyclododecane compound as claimed in claim 1, wherein the hydrogenation is carried out under a hydrogen gas pressure of 0.8 to 9 MPa at a temperature higher than 50° C.

4. The method of producing an epoxycyclododecane compound as claimed in claim 1, wherein the platinum-containing catalytic component is present in an amount, in terms of platinum, of 0.1 to 10% by weight, based on the weight of the inert carrier component.

5. The method of producing an epoxycyclododecane compound as claimed in claim 2, wherein the platinum-containing catalytic component is present in an amount, in terms of platinum, of 0.1 to 10% by weight, based on the weight of the inert carrier component.

6. The method of producing an epoxycyclododecane compound as claimed in claim 3, wherein the platinum-containing catalytic component is present in an amount, in terms of platinum, of 0.1 to 10% by weight, based on the weight of the inert carrier component.

\* \* \* \* \*